(12) United States Patent
Potyrailo

(10) Patent No.: US 12,259,346 B2
(45) Date of Patent: Mar. 25, 2025

(54) SYSTEM AND METHOD FOR GAS SENSING

(71) Applicant: General Electric Company, Schenectady, NY (US)

(72) Inventor: Radislav Alexandrovich Potyrailo, Niskayuna, NY (US)

(73) Assignee: GE INFRASTRUCTURE TECHNOLOGY LLC, Greenville, SC (US)

( * ) Notice: Subject to any disclaimer, the term of this patent is extended or adjusted under 35 U.S.C. 154(b) by 294 days.

(21) Appl. No.: 17/859,911

(22) Filed: Jul. 7, 2022

(65) Prior Publication Data
US 2024/0011930 A1 Jan. 11, 2024

(51) Int. Cl.
*G01N 27/04* (2006.01)
*G01N 27/02* (2006.01)
*G01N 33/00* (2006.01)

(52) U.S. Cl.
CPC ......... *G01N 27/046* (2013.01); *G01N 27/026* (2013.01); *G01N 33/006* (2013.01)

(58) Field of Classification Search
CPC ... G01N 27/046; G01N 27/026; G01N 33/006
See application file for complete search history.

(56) References Cited

U.S. PATENT DOCUMENTS

| | | | |
|---|---|---|---|
| 3,625,756 A | 12/1971 | Taguchi | |
| 3,631,436 A | 12/1971 | Taguchi | |
| 4,533,520 A | 8/1985 | Bossart et al. | |
| 4,730,479 A | 3/1988 | Pyke et al. | |
| 5,418,131 A * | 5/1995 | Butts | C12M 41/48 422/123 |
| 8,802,568 B2 | 8/2014 | Mayer et al. | |
| 9,401,983 B2 | 7/2016 | Lechner et al. | |
| 9,995,593 B2 | 6/2018 | Badeja et al. | |
| 10,368,146 B2 * | 7/2019 | Potyrailo | H04Q 9/00 |

(Continued)

FOREIGN PATENT DOCUMENTS

WO 2020045738 A1 3/2020

OTHER PUBLICATIONS

Potyrailo, R. A., Multivariable sensors for ubiquitous monitoring of gases in the era of Internet of Things and Industrial Internet, Chem. Rev. 2016, 116, 11877-11923.

(Continued)

*Primary Examiner* — Justin N Olamit
(74) *Attorney, Agent, or Firm* — Fletcher Yoder, P.C.

(57) ABSTRACT

A system and a method for gas sensing while correcting for an interferent condition around a gas sensor. The gas sensor provides dielectric excitation of a gas sensing element and an interferent-compensating sensing element arranged as a single electrical circuit at a set of frequencies, measures impedance responses of the gas sensing element and the interferent-compensating sensing element to the dielectric excitation at the set of frequencies, determines, based on the impedance responses of the gas sensing element and the interferent-compensating sensing element to the dielectric excitation the identities, the respective concentrations, or a combination thereof, of at least one analyte gas of the monitored environment, corrected for one or more sensed interferent conditions of the ambient environment.

18 Claims, 10 Drawing Sheets

(56) References Cited

U.S. PATENT DOCUMENTS

| | | | |
|---|---|---|---|
| 10,436,737 B2* | 10/2019 | Sussner | G01N 29/022 |
| 10,520,481 B2 | 12/2019 | Kozlow et al. | |
| 10,812,878 B2 | 10/2020 | Potyrailo et al. | |
| 10,872,511 B2 | 12/2020 | Kim et al. | |
| 10,966,657 B2* | 4/2021 | Potyrailo | A61B 5/6823 |
| 11,287,395 B2* | 3/2022 | Itoh | G01N 27/226 |
| 2018/0136182 A1 | 5/2018 | Wang | |
| 2021/0109049 A1 | 4/2021 | Potyrailo | |

OTHER PUBLICATIONS

Li, Y.; Vancura, C.; Barrettino, D.; Graf, M.; Hagleitner, C.; Kummer, A.; Zimmermann, M.; Kirstein, K.-U.; Hierlemann, A., Monolithic CMOS multi-transducer gas sensor microsystem for organic and inorganic analytes, Sens. Actuators B 2007, 126, (2), 431-440.

Meixner, H.; Lampe, U., Metal oxide sensors, Sensors and Actuators B: Chemical 1996, 33, (1-3), 198-202.

Franke, M. E.; Koplin, T. J.; Simon, U., Metal and Metal Oxide Nanoparticles in Chemiresistors: Does the Nanoscale Matter?, Small 2006, 2, 36-50.

Korotcenkov, G.; Han, S. D.; Cho, B. K., Material Design for Metal Oxide Chemiresistive Gas Sensors, J. Sens. Sens. Techn. 2013. 22, 1-17.

Dey, A., Semiconductor metal oxide gas sensors: A review, Mater. Sci. Eng. B 2018, 229, 206-217.

Potyrailo, R. A.; Surman, C.; Nagraj, N. N.; Burns, A., Materials and Transducers Toward Selective Wireless Gas Sensing, Chem. Rev. 2011, 111, 7315-7354.

Potyrailo, R. A.; Go, S.; Sexton, D.; Li, X.; Alkadi, N.; Kolmakov, A.; Amm, B.; St-Pierre, R.; Scherer, B.; Nayeri, M.; Wu, G.; Collazo-Davila, C.; Forman, D.; Calvert, C.; Mack, C.; Mcconnell, P., Extraordinary performance of semiconducting metal oxide gas sensors using dielectric excitation, Nat. Electron. 2020, 3, 280-289.

Taicong, Y.; Tian, F.; Covington, J.A.; Xu, F.; Xu, Y.; Jiang, A.; Qian, J.; Liu, R.; Wang, Z.; Huang, Y., Resistance-Capacitance Gas Sensor Based on Fractal Geometry, Chemosensors, vol. 7, Issue-3, Jul. 15, 2019.

* cited by examiner

SYSTEM AND METHOD FOR GAS SENSING

BACKGROUND

The subject matter disclosed herein generally relates to gas sensing, and more specifically relates to gas sensing using metal oxide semiconductor (MOS) sensors.

MOS sensors can be operated as chemiresistors and are popular because of their ability to detect numerous gases with the proper selection of the base semiconductor material and doping materials. In such gas-responsive chemiresistors, a change in direct current (DC) resistance of the MOS sensing material is measured, and this change in resistance is proportional to the gas concentrations of a monitored environment. MOS-based gas sensors typically measure only a DC resistance response. A measurement of a single response per sensor under a given excitation condition is known as a single-output readout. Sensors that generate single-output readouts are known as single-output sensors.

Changes in conditions (e.g., relative humidity, temperature, barometric pressure, etc.) of the monitored environment around the MOS sensor may affect the response of the MOS sensing material to known gases. Accordingly, it may be desirable to develop a way to correct for changes in one or more conditions of the monitored environment around the MOS sensor.

BRIEF DESCRIPTION

With the foregoing in mind, present embodiments are directed to a system and a method for analysis of at least one gas using dielectric excitation, in which one or more conditions in the monitored environment are determined and accounted for. Contrary to conventional gas sensor designs, embodiments of the gas sensor disclosed herein utilize techniques for determining one or more conditions (e.g., variations of relative humidity) of the monitored environment in/around the gas sensor that may affect the outputs of the gas sensor, and then correcting measured responses of the sensor to dielectric excitation, based on the determined condition (e.g., relative humidity), to determine identities and/or concentrations of at least one gas present in the monitored environment. The disclosed gas sensors and gas sensing methods unexpectedly provide desirable characteristics, such as reliable results in a wider range of monitored environments.

For example, in an embodiment, a gas sensor for analysis of at least one gas within a monitored environment includes a sensing circuit and an impedance detector. The sensing circuit includes a gas sensing element and an interferent-compensating sensing element. The gas sensing element and the interferent-compensating sensing element are configured to contact the same monitored environment. The impedance detector is configured to provide dielectric excitation of the gas sensing element and the interferent-compensating sensing element at a set of frequencies, measure combined impedance response of the gas sensing element and the interferent-compensating sensing element to the dielectric excitation at the set of frequencies, determine, based on the combined impedance response of the gas sensing element and the interferent-compensating sensing element to the dielectric excitation identities, respective concentrations, or a combination thereof, of at least one analyte gas of the monitored environment, corrected for one or more sensed interferent conditions of the monitored environment.

In an embodiment, a method of operating a gas sensor includes exposing the gas sensor to a monitored environment, providing, via an impedance detector, to a sensing circuit comprising a gas sensing element and a humidity sensing element, a dielectric excitation of the gas sensing element and the humidity sensing element at a set of frequencies, measuring responses of the sensing circuit to the dielectric excitation at the set of frequencies, determining, based on the responses of the sensing circuit to the dielectric excitation, a relative humidity of the monitored environment; and determining, based on the responses of the sensing circuit to the dielectric excitation, identities, respective concentrations, or a combination thereof, of at least one analyte gas of the monitored environment corrected for the determined relative humidity of the monitored environment.

In an embodiment, a gas sensor for analysis of at least one gas within a monitored environment includes a sensing circuit and an impedance detector. The sensing circuit includes a gas sensing element and an interferent-compensating sensing element. The gas sensing element is configured to contact the monitored environment. The interferent-compensating sensing element is configured to contact the monitored environment. The impedance detector is configured to measure an impedance of a signal output by the sensing circuit. The impedance detector is configured to provide dielectric excitation of the sensing circuit at a set of frequencies, measure impedance responses of the sensing circuit to the dielectric excitation at the set of frequencies, determine, based on the responses of the sensing circuit to the dielectric excitation, identities, respective concentrations, or a combination thereof, of at least one analyte gas of the monitored environment, corrected for one or more sensed interferent conditions of the monitored environment.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Present embodiments are directed to a system and a method for gas sensing that determines an interferent condition (e.g., relative humidity) of the environment in which the gas sensor is disposed and corrects for the interferent condition. It may be noted that metal oxide semiconductor sensing materials are often abbreviated in the industry as metal oxide semiconductor (MOS) materials or semiconducting metal oxide (SMOX) materials. Changes in conditions (e.g., relative humidity, temperature, barometric pressure, etc.) of the monitored environment around the MOS sensor may affect the resistance response of the MOS sensing material to known gases. For example, the resistance response of a MOS sensor to a known gas when the monitored environment has a very low relative humidity may be different from the response of the MOS sensor to the known gas when the monitored environment has a very high relative humidity. Specifically, when detecting small concentrations of gases of interest, changes in relative humidity of the monitored environment can affect the resistance response of the conventional MOS sensor, thus affecting the reliability of the sensor. Conventional MOS-based gas sensors measure only a DC resistance response. A measurement of a single response per sensor under a given excitation condition is known as a single-output readout and the sensor is known as a single-output sensor. Traditionally, gas sensor systems that have the ability to correct for humidity effects, incorporate a humidity sensor in the system, where a humidity sensor is a standalone device on a separate electrical circuit from the gas sensor. In such embodiments, the separate electrical circuit for the humidity sensor typically includes a separate data collection component and separate data processing unit, resulting in increased part count, cost, footprint, and power consumption. Thus, present embodiments unexpectedly demonstrate MOS-based gas sensors that can determine characteristics or conditions of their monitored environment and correct for those characteristics or conditions to resolve identities of and/or concentrations of gases in monitored environment.

Specifically, the characteristics or conditions of the monitored environment are identified, and then the sensor responses are corrected based on the identified characteristics or conditions of the monitored environment. The identities and/or concentrations of gases present in the monitored environment can be resolved from the adjusted sensor responses as if the sensor was not affected by the characteristics or conditions of the monitored environment.

Figure 1:
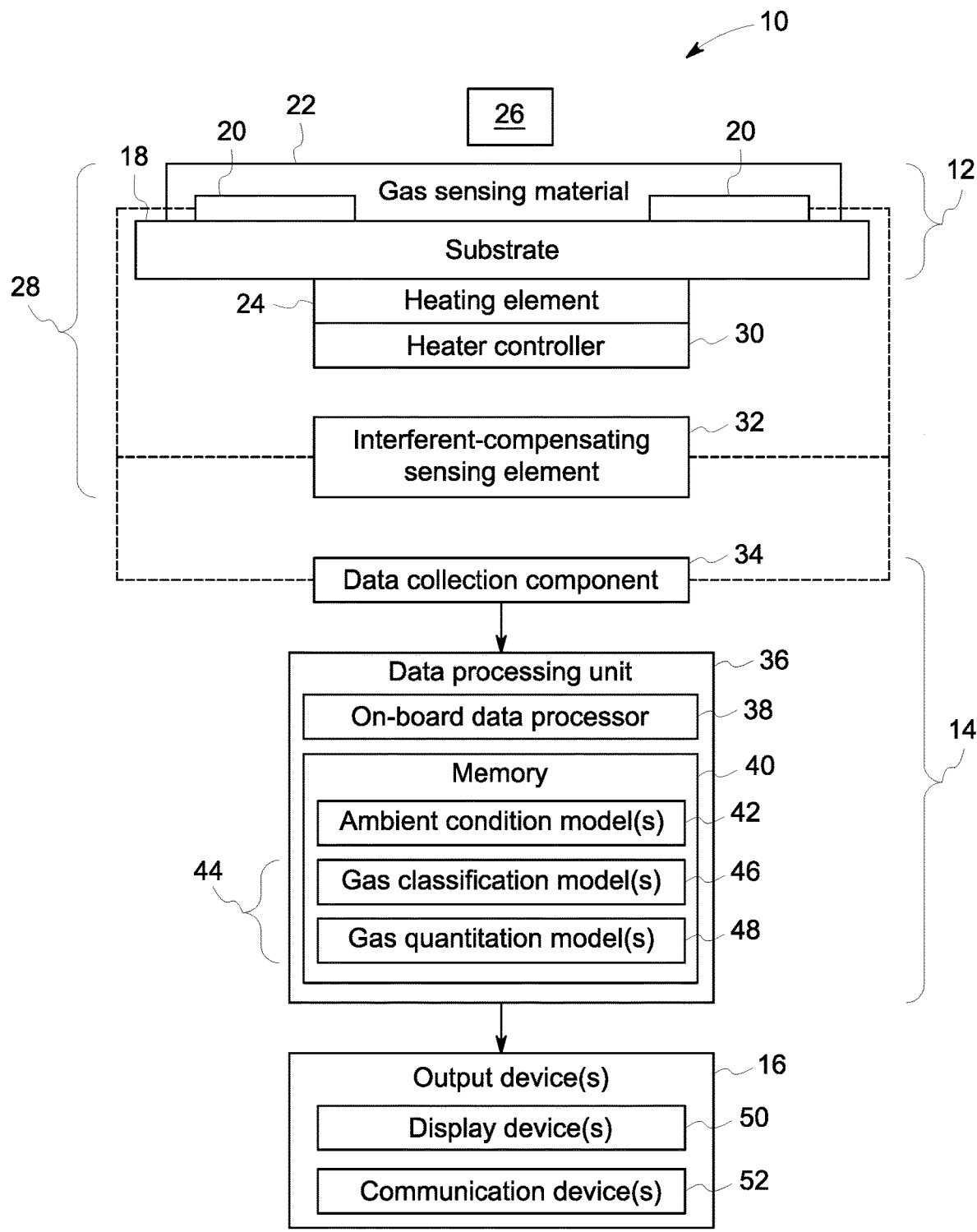
FIG. 1 is a schematic diagram of an embodiment of a gas sensor for analysis of at least one gas within a monitored environment that can correct for sensed conditions in the monitored environment, in accordance with aspects of the present technique.

With the foregoing in mind, FIG. 1 is a schematic diagram of an embodiment of a gas sensor 10 for analysis of at least one gas within a monitored environment, in accordance with the present technique. In different embodiments, the gas sensor 10 may be a wearable gas sensor, an ingestible gas sensor, a tattooed gas sensor for personal (e.g., patient) monitoring, and so forth. In certain embodiments, the gas sensor 10 may be an industrial environmental sensor, an asset monitoring sensor, an industrial process monitoring gas sensor, a consumer sensor, a transportation sensor, a security sensor, or any combination thereof. In further embodiments, the sensor may be part of a wireless sensor network.

For the embodiment illustrated in FIG. 1, the gas sensor 10 generally includes a gas sensing element 12 ( ), control circuitry 14, and one or more output devices 16. The gas sensing element 12 includes a substrate 18 having sensing electrodes 20 disposed thereon, as well as a gas sensing material 22 (e.g., a suitably doped metal oxide semiconductor material (MOS)) disposed on the substrate 18 between and/or on top of the sensing electrodes 20. In certain embodiments, there may be more than two sensing electrodes 20, and the sensing electrodes 20 may include a plurality of interdigitated sensing electrodes. In some embodiments, the gas sensing material 22 may include a perovskite oxide with two differently sized cations, or a mixed metal oxide composition, or some combination thereof.

Additionally, a resistive heating element 24 may be disposed on a surface of the substrate, opposite the gas sensing material 22, and is designed to be controlled by the heater controller 30 to heat the gas sensing material 22 to a suitable operating temperature (e.g., the temperature to which the gas sensing material 22 is heated for taking measurements) during analysis of at least one gas within a monitored environment 26. The heating element 24 may be disposed on a surface of the substrate 18, opposite the gas sensing material 22, or on the same side of the substrate 18 as the gas sensing material 22.

In some embodiments, the monitored environment 26 may be a gaseous environment. In some embodiments, the monitored environment 26 may be a fluid environment, where fluid is a gas, a liquid, or particulate matter around the gas sensor. Accordingly, the monitored environment 26 may include, for example, a gas, a liquid, a gas-liquid mixture, a solid material, particles or particulate matter, or the like, containing one or more gases, including analyte gases and/or interferent gases. In another embodiment, the monitored environment is a fluid that may be a gas or fuel, such as a hydrocarbon-based fuel. For example, the fluid may be natural gas or hydrogen gas that is supplied to a powered system (e.g., a manned vehicle, an unmanned vehicle, an airplane engine, or a stationary generator set) for consumption.

Further, the monitored environment may include gasoline, diesel fuel, jet fuel or kerosene, bio-fuels, petrodiesel-biodiesel fuel blends, natural gas (liquid or compressed), and/or fuel oils. In other embodiments, the monitored environment may be indoor or outdoor ambient air. For example, the monitored environment may be from an industrial, residential, military, construction, urban, or any other known site. Further, the monitored ambient air may include relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical agents such as nerve, blister, blood, and choking agents, hydrocarbons and/or other environmental agents. In other embodiments, the monitored environment may be a disinfecting agent, such as alcohol, aldehyde, chlorine dioxide, hydrogen peroxide, and so forth. In other embodiments, the monitored environment 26 may mix with ambient air from around the gas sensor 10 with relatively small concentrations, medium concentrations, and/or large concentrations of combustible gases such as methane, ethane, propane, butane, hydrogen, and/or other gases. The ambient air may have certain measurable or identifiable characteristics, such as relative humidity, temperature, barometric pressure, concentrations of other gases, etc. In further embodiments, the monitored environment may include at least one gas dissolved in an industrial liquid such as transformer oil, bioprocess media, fermentation media, wastewater, and so forth. The monitored environment 26 may also include at least one gas dissolved in a consumer liquid such as milk, a non-alcoholic beverage, alcoholic beverage, cosmetics, and so forth. In other embodiments, the monitored environment 26 may include at least one gas dissolved in a body liquid such as blood, sweat, tears, saliva, urine, feces, bile, and so forth. The monitored environment 26 may include analyte gases that are chemical agents, combustible gases, volatile precursors of fabrication of narcotics and substances (e.g., illegal drugs), volatile precursors of fabrication of explosives, inorganic gases, organic gases, organic vapors, oxidizing gases, reducing gases, non-condensable gases, vapors, volatile organic compounds, or any combination thereof.

In certain embodiments, the monitored environment 26 may include analyte gases that are toxic industrial materials or toxic industrial chemicals. A non-limiting list of example toxic industrial materials and chemicals includes, but is not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid (fuming), phosgene, phosphorus trichloride, sulfur dioxide, sulfuric acid, and tungsten hexafluoride. In certain embodiments, the monitored environment 26 may include analyte gases that are toxic materials of the medium Hazard Index. A non-limiting list of example toxic materials of the medium Hazard Index includes, but is not limited to: acetone cyanohydrin, acrolein, acrylonitrile, allyl alcohol, allylamine, allyl chlorocarbonate, boron tribromide, carbon monoxide, carbonyl sulfide, chloroacetone, chloroacetonitrile, chlorosulfonic acid, diketene, 1,2-dimethylhydrazine, ethylene dibromide, hydrogen selenide, methanesulfonyl chloride, methyl bromide, methyl chloroformate, methyl chlorosilane, methyl hydrazine, methyl isocyanate, methyl mercaptan, nitrogen dioxide, phosphine, phosphorus oxychloride, phosphorus pentafluoride, selenium hexafluoride, silicon tetrafluoride, stibine, sulfur trioxide, sulfuryl chloride, sulfuryl fluoride, tellurium hexafluoride, n-octyl mercaptan, titanium tetrachloride, trichloroacetyl chloride, and trifluoroacetyl chloride.

In certain embodiments, the monitored environment 26 may include analyte gases that are toxic materials of the low Hazard Index. A non-limiting list of example toxic materials of the low Hazard Index includes, but is not limited to: allyl isothiocyanate, arsenic trichloride, bromine, bromine chloride, bromine pentafluoride, bromine trifluoride, carbonyl fluoride, chlorine pentafluoride, chlorine trifluoride, chloro- acetaldehyde, chloroacetyl chloride, crotonaldehyde, cyanogen chloride, dimethyl sulfate, diphenylmethane-4,40-diisocyanate, ethyl chloroformate, ethyl chlorothioformate, ethyl phosphonothioic dichloride, ethyl phosphonic dichloride, ethyleneimine, hexachlorocyclopentadiene, hydrogen iodide, iron pentacarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl chloroformate, tert-butyl isocyanate, tetraethyl lead, tetraethyl pyrophosphate, tetramethyl lead, toluene 2,4-diisocyanate, and toluene 2,6-diisocyanate.

In certain embodiments, the monitored environment 26 may include analyte gases that are indoor pollutants. A non-limiting list of example indoor pollutants includes, but is not limited to: acetaldehyde, formaldehyde, 1,3-butadiene, benzene, chloroform, methylene chloride, 1,4-dichlorobenzene, perchloroethylene, trichloroethylene, naphthalene, and polycyclic aromatic compounds. In certain embodiments, the monitored environment 26 may include analyte gases that are outdoor pollutants. A non-limiting list of example outdoor pollutants includes, but is not limited to: ozone, nitrogen dioxide, sulfur dioxide, and carbon monoxide.

During operation of the gas sensor 10, the gas sensing material 22 of the gas sensing element 12 is heated as the gas sensing material 22 is exposed to the monitored environment 26, which may include one or more gases, including one or more analyte gases and/or one or more interferent gases. As such, the control circuitry 14 of the illustrated gas sensor 10 includes a heating controller 30 that is electrically coupled to the heating element, and that controls the heating element 24 to achieve one or more operating temperatures at which measurements are taken.

As shown, the gas sensor also includes an interferent-compensating sensing element 32, which may output a signal indicative of one or more characteristics of the monitored environment 26 around the gas sensor 10. These characteristics may include, for example, relative humidity, temperature, atmospheric pressure, particulate pollutants, gaseous pollutants and so forth. For example, the interferent-compensating sensing element 32 may be a capacitive and/or resistive sensing element, or other type of sensing element wherein the measured electrical property of the interferent-compensating sensing element 32 corresponds to a relative humidity of the monitored environment 26 around the gas sensor 10. The interferent-compensating sensing element 32 may be any passive two-terminal electrical sensing element that is designed to be responsive to a change in the ambient environment. The categories of passive two-terminal electrical sensing elements that are responsive to a change in the monitored environment may be a capacitor, a resistor, an inductor, or a memristor. The interferent-compensating sensing element 32 may be an ambient environment sensing element For the illustrated embodiment, the sensing electrodes 20 of the gas sensing element 12 and the interferent-compensating sensing element 32 are electrically coupled, in parallel, to a data collection component 34 of the control circuitry 14 of the gas sensor In some embodiments, the data collection component 34 is designed to provide at least dielectric excitation (using alternating current) to the gas sensing element 12 and the interferent-compensating sensing element 32 at preselected frequencies and to measure dielectric responses of the gas sensing element 12 (e.g., impedance responses) and the interferent-compensating sensing element 32 at these excitation frequencies. Thus, in certain embodiments, the data collection component 34 may be an impedance detector. In certain embodiments, the sensing circuit may additionally be capable of providing direct current (DC) excitations to the gas sensing element 12 and/or the interferent-compensating sensing element 32, and to measure the DC responses (e.g., resistance responses) of the gas sensing element 12 and/or the interferent-compensating sensing element 32 to these excitations. In certain embodiments, the data collection component 34 may measure both alternating current (AC) and DC responses of the gas sensing element 12 and the interferent-compensating sensing element 32. However, in certain embodiments, the sensing circuit may be designed to only provide dielectric excitation to, and only measure dielectric responses of, the gas sensor 10. element The control circuitry 14 of the illustrated gas sensor 10 includes a data processing unit 36 (also referred to herein as data processing circuitry) that is communicatively coupled to the data collection component 34 to receive the excitation responses measured by the data collection component 34. The data processing unit 36 includes a data processor 38 and a memory 40 storing ambient condition models 42 and gas analysis models 44, including analyte gas classification models 46, analyte gas quantitation models 48, or any combination thereof. The ambient condition models 42 may be mathematical models that model relationships between excitation responses (e.g., dielectric excitation responses) and ambient conditions in and around the gas sensor 10. As is described in more detail below, once the ambient condition is known, excitation responses can be corrected (e.g., via a transfer function, a coefficient multiplier, a model, a multivariate statistical model, a machine learning model, and artificial intelligence model, etc.) to resolve identities and/or concentrations of gases in the monitored environment 26.

As discussed below, the data processor 38 receives the excitation responses measured by the data collection component 34 34, selects a set of excitation responses (e.g., dielectric excitation responses) for analysis, and provides these excitation responses as inputs to one or more of the ambient condition models 42, wherein the ambient condition models 42 return outputs that identify an ambient condition in and around the gas sensor 10, and outputs that resolve one or more analyte gases of the monitored environment 26. The ambient condition models 42 may be based on multivariate statistical models, machine learning models, and artificial intelligence models. As used herein, "resolving" one or more analyte gases of a monitored environment, or "providing resolution" between one or more analyte gases of a monitored environment, refers to determining a respective classification for each of the analyte gases of the monitored environment, determining a respective concentration of the analyte gases of the monitored environment, or determining both respective classifications and respective concentrations of analyte gases of the monitored environment. As used herein, "classifying" or "determining a classification of" an analyte gas refers to determining an exact chemical identity (e.g., methanol, ethanol, propanol) of the analyte gas or determining a chemical class (e.g., a hydrocarbon, alcohol, phenol, ether, aldehyde, ketone, carboxylic acid, ester, and so forth) to which each analyte gas belongs. As used herein, an "unselected" or "non-selected" response refers an excitation response that is measured by the impedance detector 34 and is not used by the data processor 38 during analysis to resolve the analyte gases of the monitored environment 26. In some embodiments, the non-selected response may be the resistance response. For example, the non-selected response may be resistance responses at the same or different temperatures.

In certain embodiments, the memory 40 may be integrated into the data processor 38. In certain embodiments, the data processor 38 may be a multicore processor. For example, in some embodiments, the data processor 38 may be a multicore processor on a single integrated circuit with two or more separate processing units (or cores), each of which reads and executes program instructions. In certain embodiments, the multicore processor may only include a single central processing unit (CPU) and multiple additional cores. For embodiments in which the data processor 38 is a multicore processor, different ambient condition models 42, gas analysis models 44, and/or different signal processing algorithms may be independently executed by different cores to reduce the power consumption of the data processing unit 36 and/or the gas sensor 10.

For the illustrated embodiment, the gas sensor 10 includes one or more output devices 16. In certain embodiments, the output devices 16 may include one or more display devices 50 that are configured to present information regarding analysis of a monitored environment, such as the ambient condition, as well as the classification and/or concentration of one or more analyte gases of the monitored environment 26. In some embodiments, other output devices 16 (e.g., speakers, light emitting diodes (LEDs), haptic feedback devices) may be included. Accordingly, the output devices 16 may be configured to generate alarms (e.g., visual alarms, audible alarms, haptic alarms, etc.) when certain conditions are detected. In certain embodiments, the output devices 16 may include one or more communication devices 52 (e.g., wired communication interfaces, wireless communication interfaces) that enable the gas sensor 10 to communicate with other computing systems, such as a desktop computer, a mobile computing device (e.g., a laptop, smart phone), a remote server (e.g., an Internet server, a cloud server), or other sensors (e.g., gas sensors, temperature sensors, vibration sensors, health monitors) of a multi-sensor monitoring system. For example, in certain embodiments, information determined by the data processor 38 regarding the ambient condition around the gas sensor 10, and/or the resolution of one or more analyte gases in the monitored environment 26, may be provided to an external computing system that serves as a controller of a mesh of sensors that includes the gas sensor 10. In some embodiments, the gas sensor 10 may additionally or alternatively use the communication devices 52 to provide excitation response measurements to an external computing system, such that the external computing system can use these measurements to calculate one or more coefficient values for one or more of the gas analysis models and return these coefficient values to the gas sensor 10 for storage in the memory 40. Additionally, in some embodiments, the illustrated gas sensor 10 may include a battery (not shown) that is electrically coupled to provide power to various components of the gas sensor 10, including the control circuitry 14 and the output devices 16.

In some embodiments, the sensor 10 system may be a wearable device that may be worn or otherwise moved from place to place by an operator. In such embodiments, the gas sensor 10 may be positioned in or be an integrated part of a helmet, hat, glove, or other articled of clothing/equipment. For example, the gas sensor 10 may be disposed within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a piece of fabric of clothing, can be positioned on clothing, such as on a pocket, in an arm band, worn on a wrist, or other extremity, and the like. The wearable gas sensor 10 can be fabricated using manufacturing technologies based on complementary metal-oxide-semiconductor electronics, flexible electronics, flexible hybrid electronics, and other approaches to provide conformal and flexible designs, implementations, and use. Optionally, the system may be a stationary device, may be independently mobile (e.g., detachable from an operator and capable of moving independent of the operator), may be airborne, and so forth.

In one or more embodiments, the gas sensor 10 may be a wearable sensor system, may be held within a wearable and/or non-wearable transferrable object (e.g., a frame of military or industrial eyeglasses), or the like. The wearable gas sensor 10 may be worn by a subject, such as a human or animal or a robot, may be removably coupled or integrated with an article worn by a subject (e.g., a shirt, pants, safety vest, safety personal protection clothing, eyeglasses, hat, helmet, hearing device, etc.), or may be any alternative device that may be transferrable such that gas sensor 10 can be moved between different positions, may be stationary or substantially stationary, or the like. In some embodiments, the gas sensor 10 may be integrated into a mobile electronic device, a medical physiological electronic device, an audio headset electronic device, a piece of textile, or any combination thereof.

The gas sensor 10 may be in contact with the monitored environment 26 in the form of a fluid vessel that may have controlled volume or an open area, such as an indoor facility (e.g., a room, a hall, a house, a school, a hospital, a confined space, or the like), or in an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, a city, urban environment, marine environment, and so forth). In some embodiments, the gas sensor 10 may provide continuous monitoring of the monitored environment 26 within the reservoir or flow path. In one or more embodiments, the gas sensor 10 may be an impedance gas sensor, an electromagnetic sensor, an electronic sensor, a hybrid sensor, or another type of sensor. Optionally, the gas sensor 10 may be a sensor array. The gas sensor 10 that includes the gas sensing element 12 may be a multivariable gas sensor.

A gas sensing element 12 that has two or more responses or outputs may be referred to as a multivariable gas sensing element 12. Multivariate data processing principles may be applied to analyze outputs from a multivariable gas sensing element 12. Specifically, multivariate data processing principles can be applied to quantify diversity of responses of a multivariable sensor to different gases in a monitored environment 26. Further, multivariate transfer functions can be built to quantify different gases and implemented to quantify different gases in new measurement data collected from a multivariable gas sensing element 12.

Nonlimiting examples of multivariate data processing principles include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis algorithms include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Nonlimiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), or Artificial Neural Network Analysis (ANN). In certain aspects of the inventive subject matter described herein, a classification algorithm can be followed by quantitation algorithm.

In some embodiments, the sensor 10 may be implemented in applications such as outdoor/indoor air quality, homeland security, industrial safety, environmental monitoring, process control, disease diagnostics, etc. In other embodiments, the sensor may be used to detect toxic household and/or industrial chemical, environmental emissions, and/or industrial emissions. In further embodiments, the sensor 10 may be used for detection of volatiles in exhaled breath, inside a gastrointestinal tract, intestinal gas production, volatolomics, and from other emission sources from humans. Accordingly, the analyte gases may be idicative of indoor air quality, outdoor air quality, urban air pollution, transportation cabin air quality, transportation exhausts, industrial safety, homeland security, medical diagnostics, food freshness, product quality, breath analysis, breath biomarkers, or any combination thereof.

The wearable sensor 10 may be worn, or otherwise carried, by different subjects or individuals, such as, but not limited to, soldiers, medical professionals, athletes, system operators, students, otherwise active or inactive individuals, or the like. Optionally, the wearable gas sensor 10 may be coupled with, integrated with, disposed on, or the like, an asset, such as a moving system such as a drone, a stationary system, or the like. The wearable gas sensor 10 may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like.

The gas sensor 10 may represent one or more different versions of sensing systems described herein. In one or more embodiments, the sensing circuit may be a resistor-capacitor (RC) electrical circuit that includes one or more resistive and capacitive components that may be changed by the presence of one or more analyte gases of interest and/or by changing atmospheric conditions. Impedance measurements may be performed at one or more different frequencies or at one or more different RC configurations of the data collection component 34. As used herein, the term impedance is a non-limiting term for any electrical response of the gas sensing element 12 to an alternating electrical current applied to the gas sensing element 12. Such response may be measured as different electrical properties. Non-limiting examples of these different electrical responses of the gas sensing element 12 to alternating electrical current include real part of impedance ($Z'$), imaginary part of impedance ($Z''$), admittance, reactance, susceptance, and the like. In the present specification, examples of the responses are given as real part of impedance ($Z'$) and imaginary part of impedance ($Z''$), however, other electrical responses of the gas sensing element 12 to alternating electrical current are also envisaged.

In the illustrated embodiment, the gas sensing element 12 is an analog gas sensing element 12, the interferent-compensating sensing element 32 is an analog interferent-compensating sensing element 32. The gas sensing element 12 and the interferent-compensating sensing element 32 may be electrically coupled to one another to form a single gas sensor 10. However, embodiments are also envisaged in which the gas sensing element 12, the interferent-compensating sensing element 32, or both, are digital components.

Figure 2:
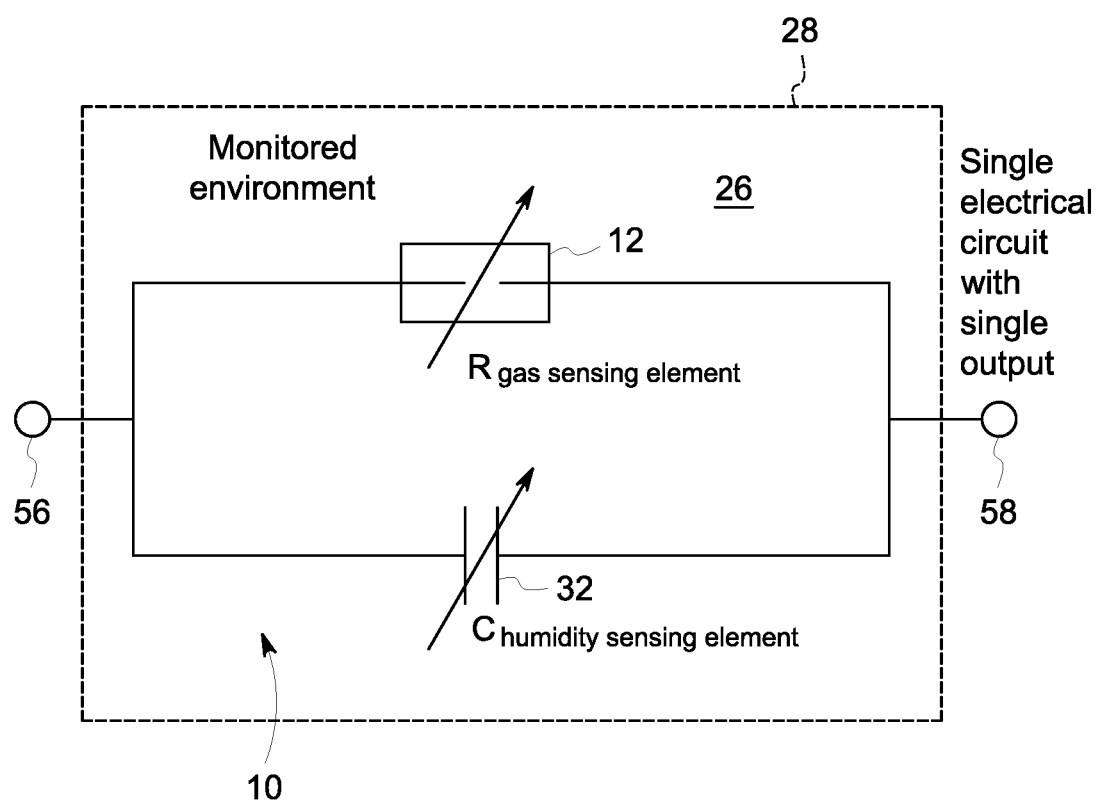
FIG. 2 is a schematic diagram of an embodiment of the gas sensor of FIG. 1, illustrating an analog gas sensing element and an analog humidity sensing element in parallel in a single electrical circuit, in accordance with aspects of the present technique.

FIG. 2 is a schematic view of an embodiment of the gas sensor 10 in which the interferent-compensating sensing element 32 is a humidity sensing element. As shown, the gas sensing element 12 and the humidity sensing element (interferent-compensating sensing element 32) are connected in parallel, forming a single two-terminal electrical sensing circuit 28, having a first terminal 56 and a second terminal 58. As shown, the sensing circuit 28 resembles a resistor-capacitor (RC) circuit in which the gas sensing element 22 resembles a resistor, and the interferent-compensating sensing element 32 resembles a capacitor. In some embodiments, the gas sensing element 22 may also have a capacitive component (not shown), and the interferent-compensating sensing element 32 may also have a resistive component (not shown).

The gas sensing element 12 may be a multivariable gas sensing element because dielectric excitation measurements (e.g., impedance measurements) are performed at two or more excitation frequencies. The single electrical sensing circuit 28 may include an analog metal oxide gas sensing element and an analog capacitive humidity sensing element that may be electrically coupled to one another in parallel.

Dielectric excitation may be applied to terminals 56 and 58 of the two-terminal sensing circuit 28. The response of the sensing circuit 28 to the dielectric excitation is measured from the terminals 56 and 58 that may have a resistive component and a capacitive component that represents the presence and/or concentration of various gases in a monitored environment and the relative humidity in the monitored environment 26 around the gas sensor 10. Accordingly, the impedance response to the dielectric excitation, as measured from the terminals 56 and 58, may simultaneously provide information about the presence and/or concentration of various gases in the monitored environment 26 and the humidity around the gas sensor 10.

The presently disclosed techniques may be used to accurately differentiate between the presence and/or concentration of various gases in the monitored environment 26 and the relative humidity in the monitored environment 26 around the gas sensor 10 by providing dielectric excitation of the gas sensor 10 at several frequencies, obtaining responses the gas sensor 10 at several frequencies, and building transfer functions that separately predict the presence and/or concentration of various gases in a monitored environment 26 and separately predict the relative humidity around the gas sensor 10.

By combining the gas sensing gas sensing element 12 and the interferent-compensating sensing element 32 into a single electrical circuit 28, the number of components in the gas sensor 10 may be substantially reduced, thus reducing part count, cost footprint, power consumption, etc. For example, by combining the gas sensing element 12 and the interferent-compensating sensing element 32 into a single electrical circuit 28, the gas sensor 10 omits a second electrical circuit for sensing various aspects of the monitored environment, a second data collection component for the second electrical circuit, and a second data processing unit for the second electrical circuit. As such, a single electrical circuit 28, data collection component 34, and data processing unit 36 can collect and analyze an output from the single output of the electrical circuit 28, which provides information about the presence and/or concentration of various gases in a monitored environment 26 and the humidity in the monitored environment 26 around the gas sensor 10.

Figure 3:
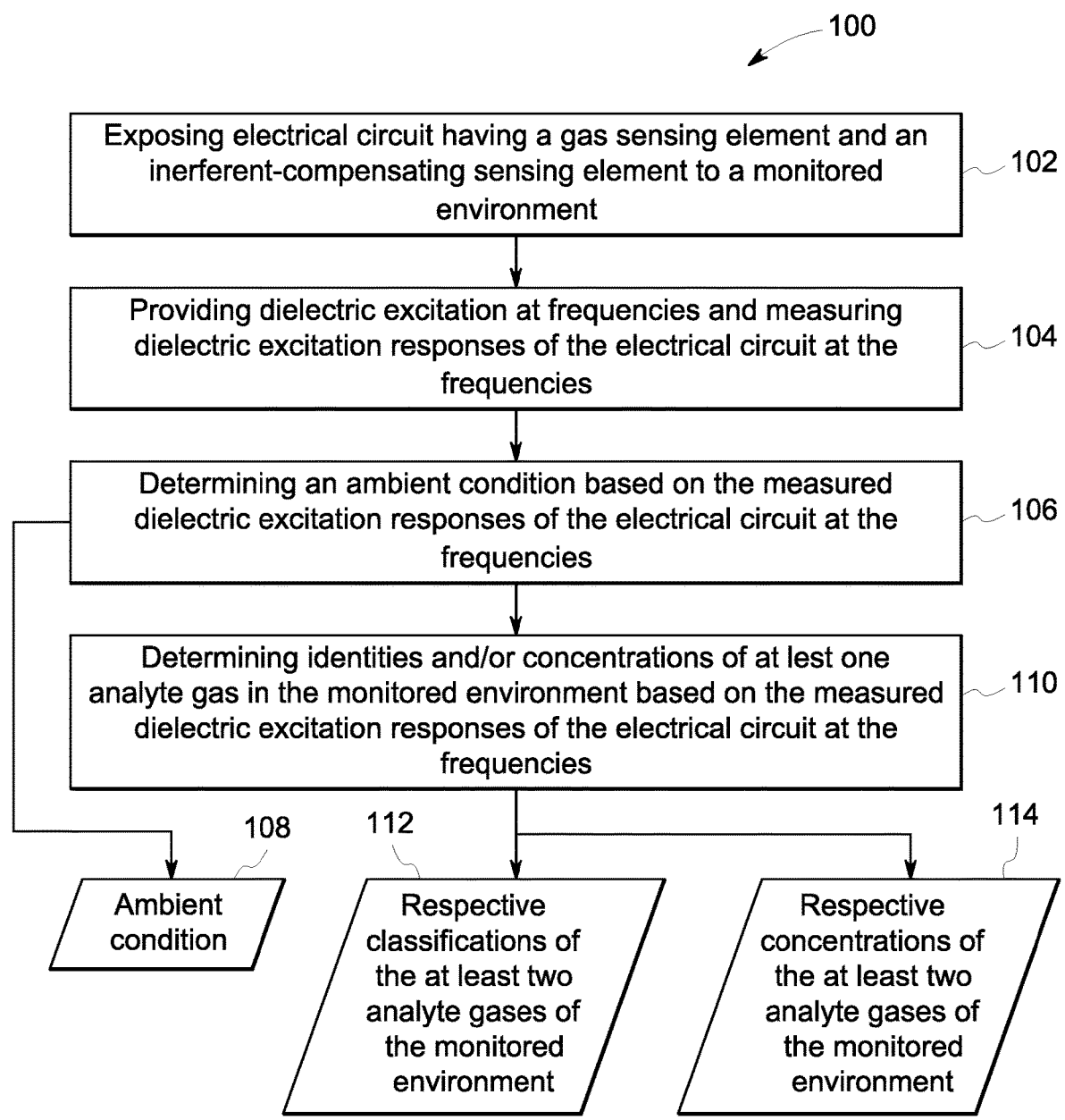
FIG. 3 is a flow diagram illustrating an embodiment of a process whereby the gas sensor performs analysis of at least one gas within a monitored environment while correcting for sensed conditions in the monitored environment, in accordance with aspects of the present technique.

FIG. 3 is a flow diagram illustrating an embodiment of a process 100 whereby the gas sensor 10 performs gas analysis of the monitored environment 26. The process 100 begins with exposing (block 102) an electrical circuit having a gas sensing element 12 and interferent-compensating sensing element 32 to a monitored environment 26 having at least two gases, including one or more analyte gases and/or one or more interferent gases.

At block 104, the data collection component 34 provides dielectric excitation using preselected frequencies to the gas sensing element 12 and the interferent-compensating sensing element 32 and measures dielectric excitation responses (e.g., impedance responses) of gas sensing element 12 and interferent-compensating sensing element 32. As discussed in more detail below, the dielectric excitation responses of the gas sensor 10 may be indicative of ambient conditions in the monitored environment 26 around that gas sensor 10, and identities and/or concentrations of analyte gases in the monitored environment, when taking into consideration the ambient conditions in the monitored environment 26 around that gas sensor 10. In certain embodiments, the data collection component 34 may additionally apply DC excitation to the gas sensing element 12 and the interferent-compensating sensing element 32 and measure DC excitation responses (e.g., resistance responses) of the gas sensing element 12 and the interferent-compensating sensing element 32. However, in some embodiments, the data collection component 34 may be an impedance detector and may only measure dielectric excitation responses of the gas sensing element 12 and the interferent-compensating sensing element 32 as it contacts the monitored environment 26.

Traditionally, MOS gas sensors 10 measure a DC resistance response of a MOS-based sensing element 12 and relate the measured DC resistance response to a concentration of a gas using a power-law relation between the measured resistance and gas concentration. Such DC resistance responses from a MOS gas sensor 10 may be provided as a signal output (e.g., to a user) in a form of an analog signal. Depending on the design of an analog circuit, an analog signal from a MOS gas sensor 10 may represent linear resistance, logarithmic resistance, or conductivity. Alternatively DC resistance responses from a traditional MOS-based gas sensor 10 may be provided as a signal output in a form of a digitized DC resistance response signal. Dependent upon the design of an analog/digital circuit, the digital signal from a MOS gas sensor 10 may be correlated with linear resistance, logarithmic resistance, or conductivity. A digital signal from a MOS gas sensor 10 that is correlated with its DC resistance response can be provided (e.g., to the user) by any of digital communication protocols, for example an I2C (Inter-Integrated Circuit), alternatively known as IIC, and any other communication protocols.

At block 106, the data processor 38 of the gas sensor 10 performs data analysis of the dielectric excitation responses based on at least one of the ambient condition models 42 to determine and output one or more ambient conditions 108 of the monitored environment 26 around the gas sensor 10. As discussed previously with regard to FIG. 1, the ambient condition 108 may be determined by applying one or more ambient condition models 42 (e.g., mathematical models) that model relationships between excitation responses and ambient conditions (e.g., relative humidity) in the monitored environment 26 around the gas sensor 10. In some embodiments, this may involve evaluating the excitation responses at multiple frequencies to identify one or more frequencies at which the different ambient conditions are discernable. In some embodiments, the ambient condition 108 may be a value that indicates the ambient condition 108 around the gas sensing element 12, which may be applied to the excitation responses to generate corrected responses such that identities and/or concentrations of gases in the monitored environment 26 can be determined. In other examples, the ambient condition 108 may be provided to a transfer function, a lookup table, a model, a coefficient multiplier, etc. to generate corrected excitation responses, from which identities and/or concentrations of gases in the monitored environment 26 can be determined. In some embodiments, the transfer function, the lookup table, and/or the model, etc. may be selected based on the determined ambient condition 108 in the monitored environment 26 around the gas sensor 10. In other embodiments, the transfer function may be generated and/or updated based upon the determined ambient condition 108. In some embodiments, the transfer function may be generated based on an imaginary part of impedance spectra, a real part of impedance spectra, or both. The real and/or imaginary parts of the impedance spectra may be generated based on the dielectric excitation at the set of frequencies. Further, the transfer function may be updated when new data is collected, on a periodic basis, upon some triggering event taking place, and so forth. Accordingly, recalibration of the transfer function may occur on a periodic basis, as opposed to being part of a standard measurement cycle. Sensor analysis is performed on a cyclical basis (such as monthly, annually, every three years, etc.) and changes in measurement performance may be corrected based on a recalibration.

At block 110, the data processor 38 of the gas sensor 10 performs data analysis of the dielectric excitation responses based on the determined ambient condition 108 of the gas sensor 10, as well as at least one of the stored gas analysis models 44 to provide a real-time resolution of the analyte gases of the monitored environment 26. That is, at block 110, the system may output respective classifications of one or more analyte gases within the monitored environment 112 and/or respective concentrations of one or more analyte gases within the monitored environment 114. For certain embodiments in which DC excitation responses are also measured by the data collection component, the data processor 38 may also provide these DC excitation responses as inputs to at least one of the ambient condition models 42, and/or the stored gas analysis models 44 when resolving the analyte gases of the monitored environment. In this context, "real-time" refers to the data processor 38 of the gas sensor 10 being able to locally, rapidly resolve analyte gases of the monitored environment without requiring the measured excitation responses to be provided to an external computing system for processing. For example, in some embodiments, the data processing unit 36 may be configured to identify one or more frequencies at which the response of the gas sensing material to the dielectric excitation is linear or substantially linear (e.g., the coefficient of determination value of the linear fit is greater than 0.9, 0.95, 0.96, 0.97, 0.98, 0.99, etc.). The data processing unit 36 may then generate or select and apply a transfer function (e.g., based on the determined ambient condition 108) to the data collected from the response of the gas sensing material to the dielectric excitation at the one or more frequencies of the set of frequencies to generate corrected response data that corrects for ambient condition. However, in other embodiments, a multiplier coefficient, a lookup table, a model, etc. may be applied to the data collected from the response of the gas sensing material to the dielectric excitation to correct for and/or account for the ambient condition around the sensor 10.

The analyte gases may include a wide range of materials and/or chemicals of various hazard indexes. Materials having a "high" hazard index may include, for example, Ammonia, Arsine, Boron trichloride, Boron trifluoride, Carbon disulfide, Chlorine, Diborane, Ethylene oxide, Fluorine, Formaldehyde, Hydrogen bromide, Hydrogen chloride, Hydrogen cyanide, Hydrogen fluoride, Hydrogen sulfide, Nitric acid, fuming, Phosgene, Phosphorus trichloride, Sulfur dioxide, Sulfuric acid, and Tungsten hexafluoride.

Materials having a "medium" hazard index may include, for example, Acetone cyanohydrin, Acrolein, Acrylonitrile, Allyl alcohol, Allylamine, Allyl chlorocarbonate, Boron tribromide, Carbon monoxide, Carbonyl sulfide, Chloroacetone, Chloroacetonitrile, Chlorosulfonic acid, Diketene, 1,2-Dimethylhydrazine, Ethylene dibromide, Hydrogen selenide, Methanesulfonyl chloride, Methyl bromide, Methyl chloroformate, Methyl chlorosilane, Methyl hydrazine, Methyl isocyanate, Methyl mercaptan, Nitrogen dioxide, Phosphine, Phosphorus oxychloride, Phosphorus pentafluoride, Selenium hexafluoride, Silicon tetrafluoride, Stibine, Sulfur trioxide, Sulfuryl chloride, Sulfuryl fluoride, Tellurium hexafluoride, n-Octyl mercaptan, Titanium tetrachloride, Trichloroacetyl chloride, and Trifluoroacetyl chloride.

Materials having a "low" hazard index may include, for example, Allyl isothiocyanate, Arsenic trichloride, Bromine, Bromine chloride, Bromine pentafluoride, Bromine trifluoride, Carbonyl fluoride, Chlorine pentafluoride, Chlorine trifluoride, Chloroacetaldehyde, Chloroacetyl chloride, Crotonaldehyde, Cyanogen chloride, Dimethyl sulfate, Diphenylmethane-4,40-diisocyanate, Ethyl chloroformate, Ethyl chlorothioformate, Ethyl phosphonothioic dichloride, Ethyl phosphonic dichloride, Ethyleneimine, Hexachlorocyclopentadiene, Hydrogen iodide, Iron pentacarbonyl, Isobutyl chloroformate, Isopropyl chloroformate, Isopropyl isocyanate, n-Butyl chloroformate, n-Butyl isocyanate, Nitric oxide, n-Propyl chloroformate, Parathion, Perchloromethyl mercaptan, sec-Butyl chloroformate, tert-Butyl isocyanate, Tetraethyl lead, Tetraethyl pyrophosphate, Tetramethyl lead, Toluene 2,4-diisocyanate, and Toluene 2,6-diisocyanate. Analyte gases may also include a range of indoor environmental agents, such as Acetaldehyde, Formaldehyde, 1,3-Butadiene, Benzene, Chloroform, Methylene chloride, 1,4-Dichlorobenzene, Perchloroethylene, Trichloroethylene, Naphthalene, Polycyclic aromatic compounds, as well as outdoor environmental agents, such as Ozone, Nitrogen dioxide, Sulfur dioxide, Carbon monoxide. Further, the analyte gases may include industrial agents, such as combustibles, confined space hazards, and so forth.

For the embodiment of the process 100 illustrated in FIG. 3, after resolving the analyte gases of the monitored environment 26, the gas sensor 10 may use one or more output devices 16 to output the respective classifications 112 of the analyte gases of the monitored environment, the respective concentrations 114 of the analyte gases of the monitored environment, the determined ambient condition around the gas sensor 10, or some combination thereof. For example, one or more output devices 16 of the gas sensor may present or display the respective classifications 112, the respective concentrations 114 of the analyte gases of the monitored environment 26, the ambient condition around the gas sensor 10, or some combination thereof. In certain embodiments, the gas sensor may provide the respective classifications 112, the respective concentrations 114 of the analyte gases, the ambient condition around the gas sensor 10, or some combination thereof, to an external computing system via one or more suitable communication devices 52 (e.g., a wireless communication interface) of the gas sensor 10.

Figure 4:
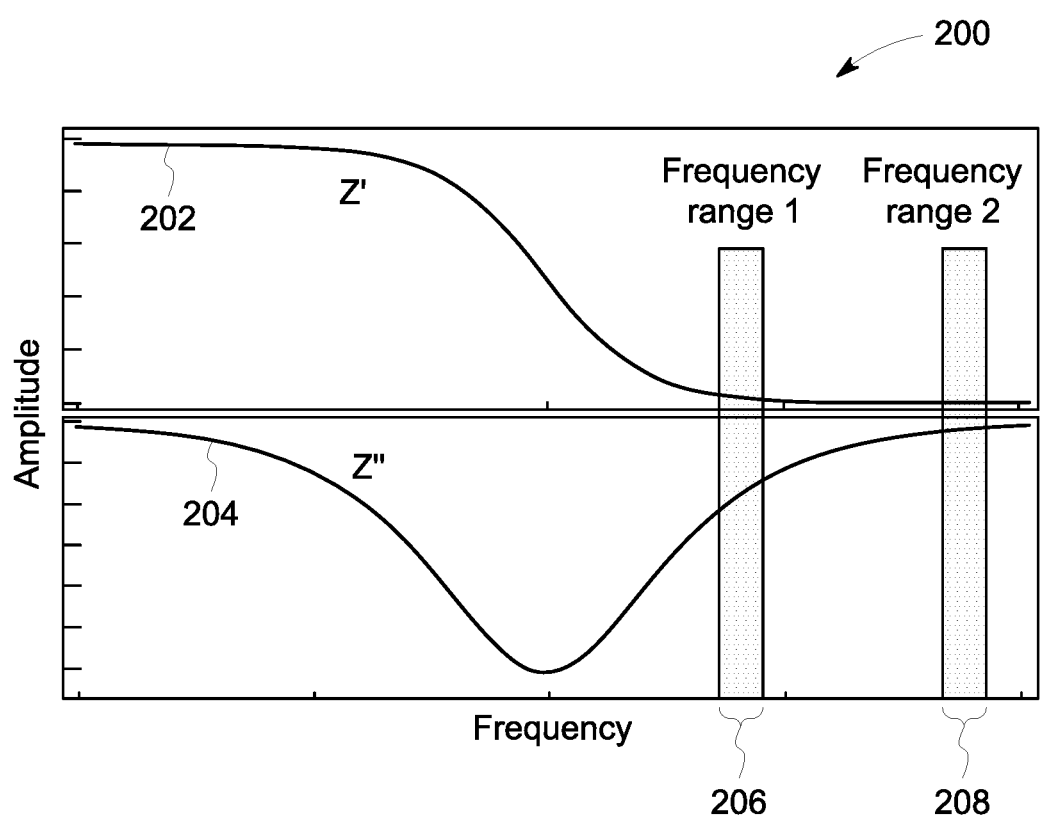
FIG. 4 is a graph of an example impedance spectrum showing the real part Z' and the imaginary part Z" of the impedance spectrum of a gas sensing material of the gas sensor of FIG. 1 with preselected frequencies for dielectric excitation, in accordance with aspects of the present technique.

FIG. 4 is a graph illustrating an example impedance spectrum 200. In impedance spectroscopy, measurements of the real part Z' and the imaginary part Z" of the impedance may be performed over a broad range of frequencies to determine the shape of the impedance spectrum 200 of the gas sensor 10. As illustrated, the impedance spectrum includes two curves, each representing part of the impedance response of the gas sensor 10 over a broad range of frequencies to determine the shape of the impedance spectrum. In particular, a first curve 202 represents the real part (Z') of the impedance of gas sensor 10, while a second curve 204 represents the imaginary part (Z") of the impedance of the gas sensor 10 as measured over a broad range of frequencies.

Unlike broad-band impedance spectroscopy measurements, the dielectric excitation measurements are performed over specific frequency ranges by following the front (high- or low-frequency) shoulder of the dielectric relaxation region obtained from impedance measurements of (n- or p-type, respectively) MOS materials when they are exposed to various gas concentrations.

In the illustrated embodiment, the data collection component 34 is an impedance detector that measures the dielectric excitation response of the gas sensor 10 at two or more frequency ranges 206, 208, which may or may not be disposed in the "dielectric relaxation region" of the gas sensor 10. For example, in certain embodiments, each dielectric excitation response measured by the impedance detector 34 may include a combination (e.g., a sum, a difference, any other mathematical representation) of a value from the first curve 202 (e.g., a real impedance value) and a value from the second curve 204 (e.g., an imaginary impedance value), both selected from the frequency ranges 206, 208. However, other embodiments may utilize data collection components 34 other than impedance detectors.

Alternatively, in some embodiments, each dielectric excitation response measured by the impedance detector 34 may include a combination (e.g., a sum, a difference, any other mathematical representation) of a value from the first curve 202 (e.g., a real impedance value Z') and a value from the second curve 204 (e.g., an imaginary impedance value Z"), both selected from the frequency ranges 206, 208, or other frequency ranges.

Selection of the frequency ranges 206, 208 may depend on a type of the gas sensing element 12 and the interferent-compensating sensing element 32 of the gas sensor For example, related to the gas sensing element 12, the selection of the frequency ranges 206, 208 may depend on the type of the MOS sensing material, for example n-type or p-type or a combination of n- and p-type MOS sensing material and type of gases for measurements such of reducing gases or oxidizing gases. As a result, either the high-frequency shoulder region or the low-frequency shoulder region may be selected for measurements.

Figure 5:
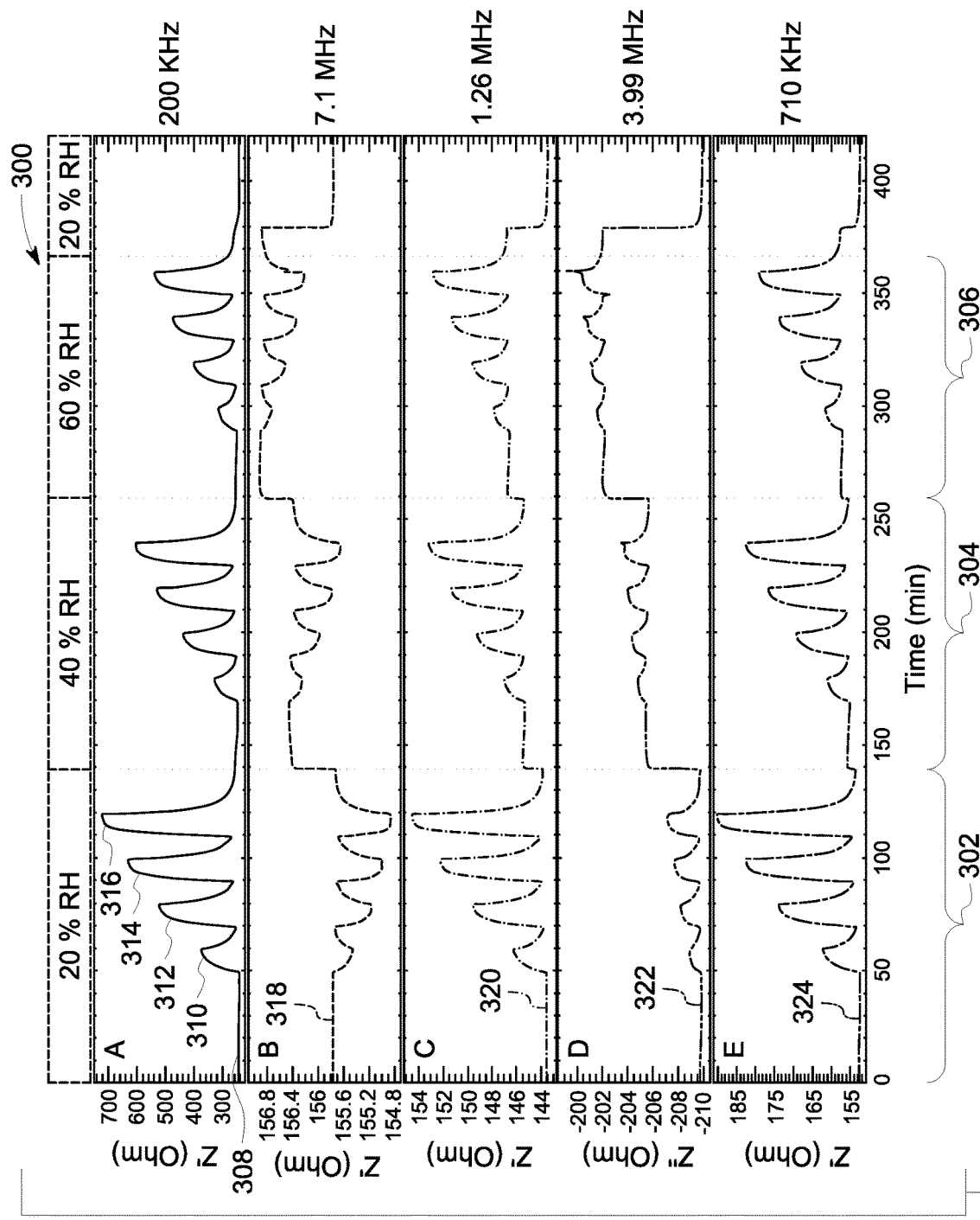
FIG. 5 is a series of Z' and Z" plots depicting response patterns of the electrical sensing circuit to four concentrations of methanol vapor at three relative humidities at five frequencies, in accordance with aspects of the present technique.

To demonstrate the performance of the disclosed techniques, experiments were performed to account for variations in relative humidity of the ambient monitored environment. The experimental setup included an electrical sensing circuit including an analog metal oxide gas sensing element and an analog capacitive humidity sensing element that were connected in parallel. The electrical sensing circuit included an analog metal oxide gas sensing element and an analog capacitive humidity sensing element connected in parallel. A single impedance detector such as an impedance analyzer was utilized to measure response of the electrical sensing circuit to the gas of interest in the presence of variable ambient humidity. The relative humidity was set to 20% and the gas sensor was exposed to four increasing concentrations of methanol vapor: 6.25 ppm, 12.50 ppm, 18.75 ppm, and 25 ppm. The relative humidity was increased to 40% and the gas sensor was again exposed to the same four increasing concentrations of methanol vapor. The relative humidity was increased to 60% and the gas sensor was once again exposed to the same four increasing concentrations of methanol vapor. The relative humidity was then reduced back to 20%. FIG. 5 includes a series of plots 300 of collected experimental data from the electrical sensing circuit at five frequencies with measured real part Z' of impedance and imaginary part Z" of impedance. The horizontal axes represent time in minutes. The vertical axes represent impedance in ohms. During a first period of time 302, the relative humidity was kept constant at 20% while the sensor was exposed to four increasing concentrations of methanol vapor: 6.25 ppm, 12.50 ppm, 18.75 ppm, and ppm. During a second period of time 304, the relative humidity was kept constant at 40% while the sensor was again exposed to the same four increasing concentrations of methanol vapor. During a third period of time 306, the relative humidity was kept constant at 60% while the sensor was again exposed to the same four increasing concentrations of methanol vapor.

Accordingly, during the first time period 302, plot 308 represents the Z' response of the electrical sensing circuit, at a frequency of 200 kHz, to a first sample having 6.25 ppm (310) concentration of methanol vapor, a second sample having 12.50 ppm (312) concentration of methanol vapor, a third sample having 18.75 ppm (314) concentration of methanol vapor, and a fourth sample having 25.00 ppm (316) concentration of methanol vapor, all at 20% relative humidity. During the second time period 304, plot 308 represents the response of the sensor, at 200 kHz, to four samples having the same four increasing levels of concentration (i.e., 6.25 ppm, 12.50 ppm, 18.75 ppm, and 25 ppm) while the relative humidity is kept constant at 40%. During the third time period 306, plot 308 represents the response of the sensor, at 200 kHz, to four samples having the same four increasing levels of concentration (i.e., 6.25 ppm, 12.50 ppm, 18.75 ppm, and 25 ppm) while the relative humidity is kept constant at 60%.

Plot 318 represents the Z' response of the electrical sensing circuit, at 7.1 MHz, to (1) four samples having the same four increasing levels of concentration (i.e., 6.25 ppm, 12.50 ppm, 18.75 ppm, and 25 ppm) while the relative humidity is kept constant at 20%, (2) four samples having the same four increasing levels of concentration (i.e., 6.25 ppm, 12.50 ppm, 18.75 ppm, and 25 ppm) while the relative humidity is kept constant at 40%, and (3) four samples having the same four increasing levels of concentration (i.e., 6.25 ppm, 12.50 ppm, 18.75 ppm, and 25 ppm) while the relative humidity is kept constant at 60%.

Plot 320 represents the response Z' of the electrical sensing circuit, at 1.26 MHz, to (1) four samples having the same four increasing levels of concentration (i.e., 6.25 ppm, 12.50 ppm, 18.75 ppm, and 25 ppm) while the relative humidity is kept constant at 20%, (2) four samples having the same four increasing levels of concentration (i.e., 6.25 ppm, 12.50 ppm, 18.75 ppm, and 25 ppm) while the relative humidity is kept constant at 40%, and (3) four samples having the same four increasing levels of concentration (i.e., 6.25 ppm, 12.50 ppm, 18.75 ppm, and 25 ppm) while the relative humidity is kept constant at 60%.

Plot 322 represents the response Z" of the electrical sensing circuit, at 3.99 MHz, to (1) four samples having the same four increasing levels of concentration (i.e., 6.25 ppm, 12.50 ppm, 18.75 ppm, and 25 ppm) while the relative humidity is kept constant at 20%, (2) four samples having the same four increasing levels of concentration (i.e., 6.25 ppm, 12.50 ppm, 18.75 ppm, and 25 ppm) while the relative humidity is kept constant at 40%, and (3) four samples having the same four increasing levels of concentration (i.e., 6.25 ppm, 12.50 ppm, 18.75 ppm, and 25 ppm) while the relative humidity is kept constant at 60%.

Plot 324 represents the response Z' of the electrical sensing circuit, at 710 kHz, to (1) four samples having the same four increasing levels of concentration (i.e., 6.25 ppm, 12.50 ppm, 18.75 ppm, and 25 ppm) while the relative humidity is kept constant at 20%, (2) four samples having the same four increasing levels of concentration (i.e., 6.25 ppm, 12.50 ppm, 18.75 ppm, and 25 ppm) while the relative humidity is kept constant at 40%, and (3) four samples having the same four increasing levels of concentration (i.e., 6.25 ppm, 12.50 ppm, 18.75 ppm, and 25 ppm) while the relative humidity is kept constant at 60%.

As shown in FIG. 5, at 200 kHz, changes in relative humidity have very little or no effect on the sensor baseline, but had a substantial effect on the magnitude of sensor response to methanol vapor such that the magnitude of the response to increasing concentrations of methanol vapor decreased as the relative humidity increased. At 7.10 MHz, responses to increasing concentrations of methanol vapor and responses to changes in relative humidity were in opposite directions. However, at other frequencies (e.g., 1.26 MHz, 3.99 MHz, and 710 kHz), responses to increasing concentrations of methanol vapor and to increasing relative humidity were in the same direction but with the different relative intensities. Accordingly, at some frequencies, changes in relative humidity may have a large effect on the response of the sensor to various concentrations of methanol vapor. As such, by evaluating sensor response at multiple frequencies, the relative humidity can be determined and corrected for to more accurately determine presence and/or concentrations of gases regardless of relative humidity using a single electrical circuit.

Figure 6:
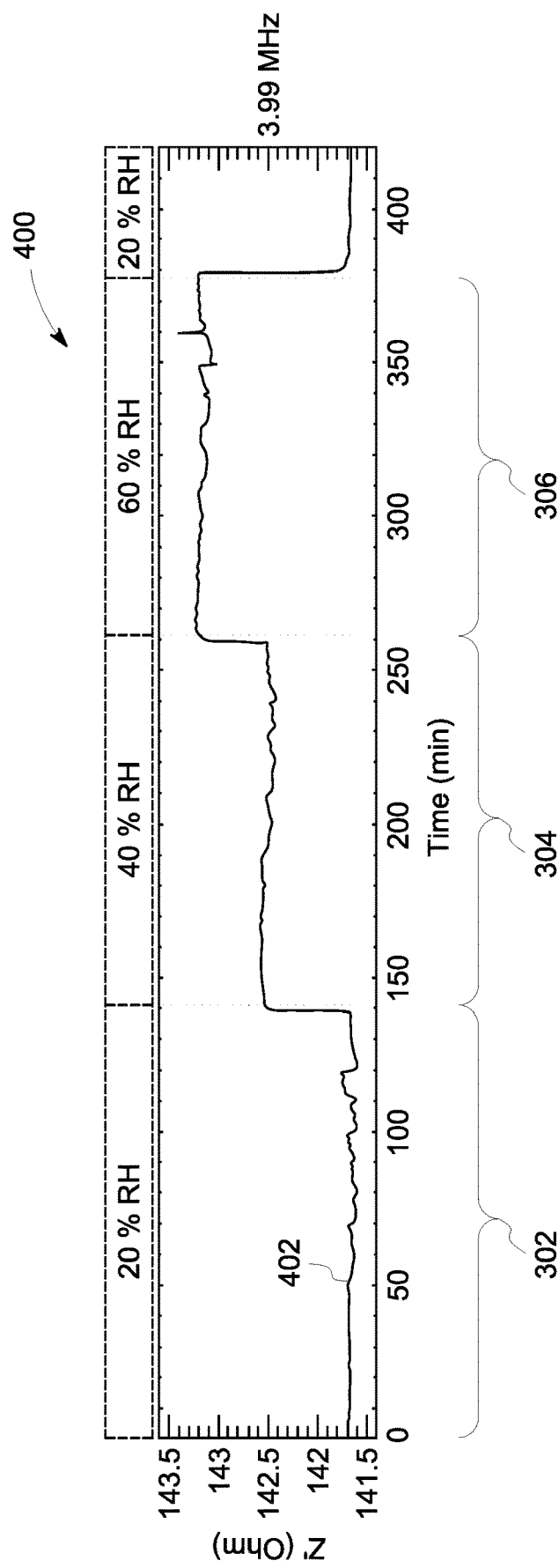
FIG. 6 is a plot of a real component (Z') of impedance response of the electrical sensing circuit to the four concentrations of methanol vapor at three relative humidities at 3.99 MHz, in accordance with aspects of the present technique.

It should be noted that though the real component (Z') of the electrical sensing circuit response is shown for all but one of the frequencies in FIG. 5, the plot 322 at 3.99 MHz is of the imaginary component (Z") of the sensor response. As shown, the changes in relative humidity have a larger effect on the response than the changes in the concentration of methanol vapor. FIG. 6 is a plot 400 of the real component (Z') of the sensor response at 3.99 MHz during the experiment described with regard to FIG. 5. That is, the sensor is exposed to (1) four samples having the same four increasing levels of concentration of methanol vapor (i.e., 6.25 ppm, 12.50 ppm, 18.75 ppm, and 25 ppm) while the relative humidity was kept constant at 20% during the first period of time 302, (2) four samples having the same four increasing levels of concentration of methanol vapor (i.e., 6.25 ppm, 12.50 ppm, 18.75 ppm, and 25 ppm) while the relative humidity was kept constant at 40% during the second period of time 304, and (3) four samples having the same four increasing levels of concentration of methanol vapor (i.e., 6.25 ppm, 12.50 ppm, 18.75 ppm, and 25 ppm) while the relative humidity was kept constant at 60% during the third period of time 306. As shown, the real component (Z') of the sensor response 402 at 3.99 MHz shows almost no effect from the changes in the concentration of methanol vapor. As such, using this data, a simple transfer function can be generated that corrects for variations in relative humidity based on responses of the same sensor at different frequencies.

Figure 7:
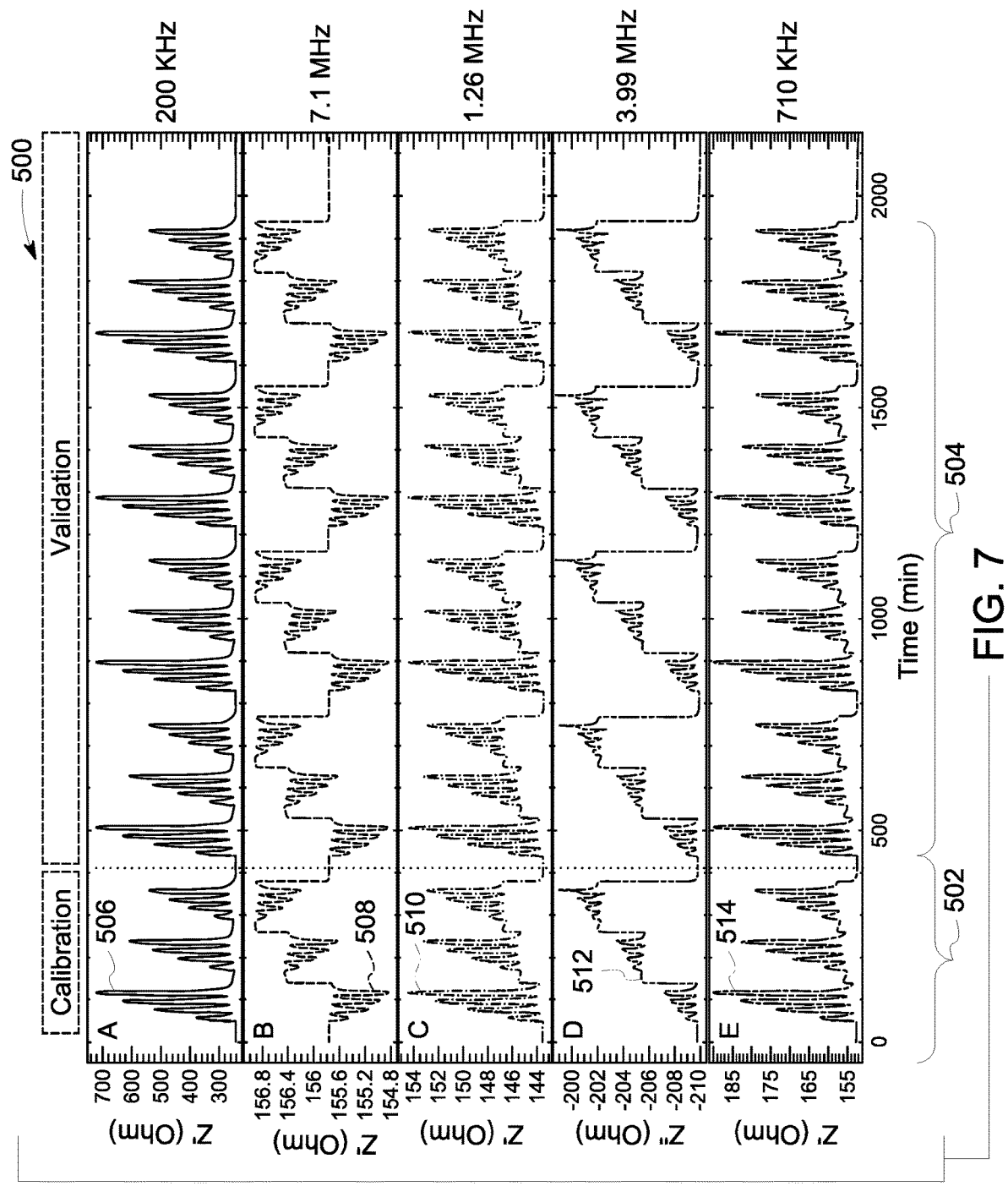
FIG. 7 is a series of Z' and Z" plots depicting response patterns of the electrical sensing circuit to the four concentrations of methanol vapor at the three relative humidities at the five frequencies during a calibration phase and a validation phase, in accordance with aspects of the present technique.
Figure 8:
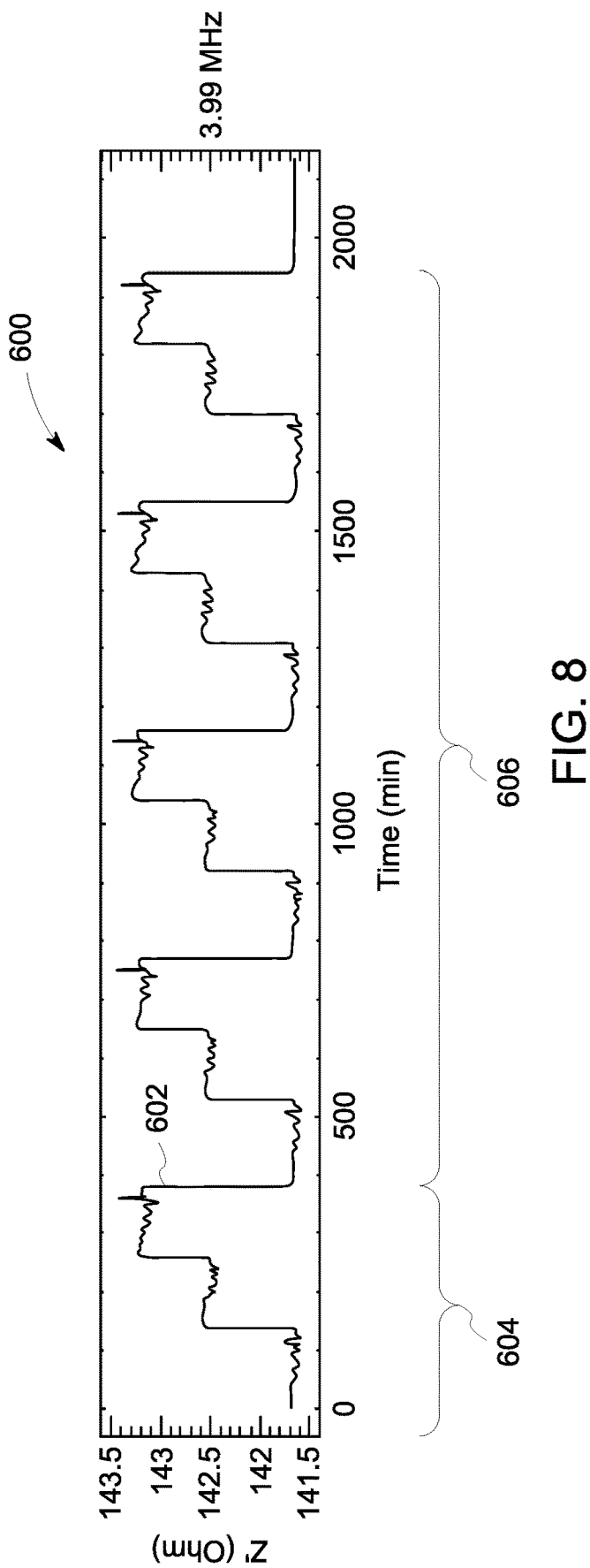
FIG. 8 is a plot of the real component (Z') of impedance of the electrical sensing circuit response to the four concentrations of methanol vapor at the three relative humidities at 3.99 MHz during the calibration phase and validation phase of FIG. 7, in accordance with aspects of the present technique.

FIG. 7 is a group of plots 500 of data during a calibration and validation test similar to the experiment shown and described with regard to FIG. 5. During a calibration phase 502, the same experiment described with regard to FIG. 5 was performed to calibrate the model. That is, the electrical sensing circuit is exposed to (1) four samples having the same four increasing levels of concentration of methanol vapor (i.e., 6.25 ppm, 12.50 ppm, 18.75 ppm, and 25 ppm) while the relative humidity was kept constant at 20%, (2) four samples having the same four increasing levels of concentration of methanol vapor (i.e., 6.25 ppm, 12.50 ppm, 18.75 ppm, and 25 ppm) while the relative humidity was kept constant at 40%, and (3) four samples having the same four increasing levels of concentration of methanol vapor (i.e., 6.25 ppm, 12.50 ppm, 18.75 ppm, and 25 ppm) while the relative humidity was kept constant at 60%. The plots 500 include responses at 200 kHz (506), 7.1 MHz (508), 1.26 MHz (510), 3.99 MHz (512), and 710 kHz (514) of Z' and Z" responses, as in FIG. 5. During the validation phase 504, the same experiment was run four additional times and compared to the model. As with FIG. the real component (Z') of the sensor response is shown for all but one of the frequencies in FIG. 7, the plot 512 at 3.99 MHz is of the imaginary component (Z") of the sensor response. As shown, and as previously discussed, the changes in relative humidity have a larger effect on the response than the changes in the concentration of methanol vapor. FIG. 8 is a plot 600 of the real component (Z') of the sensor response at 3.99 MHz during the calibration phase 604 and validation phase 606 described with regard to FIG. 7. As shown, the real component (Z') of the sensor response 602 at 3.99 MHz shows almost no effect from the changes in the concentration of methanol vapor.

Figure 9:
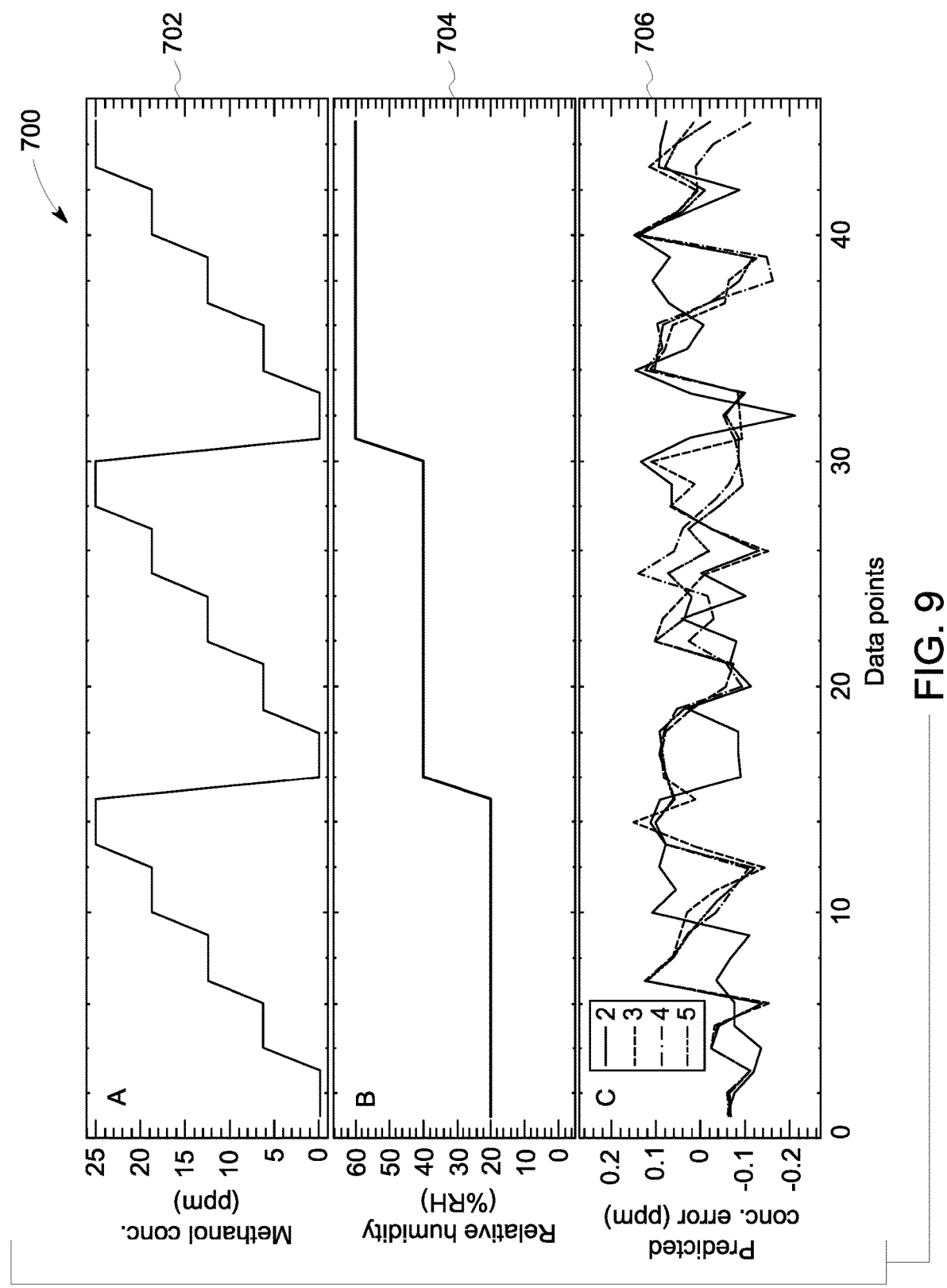
FIG. 9 is a series of plots of calibration results, in accordance with aspects of the present technique.
Figure 10:
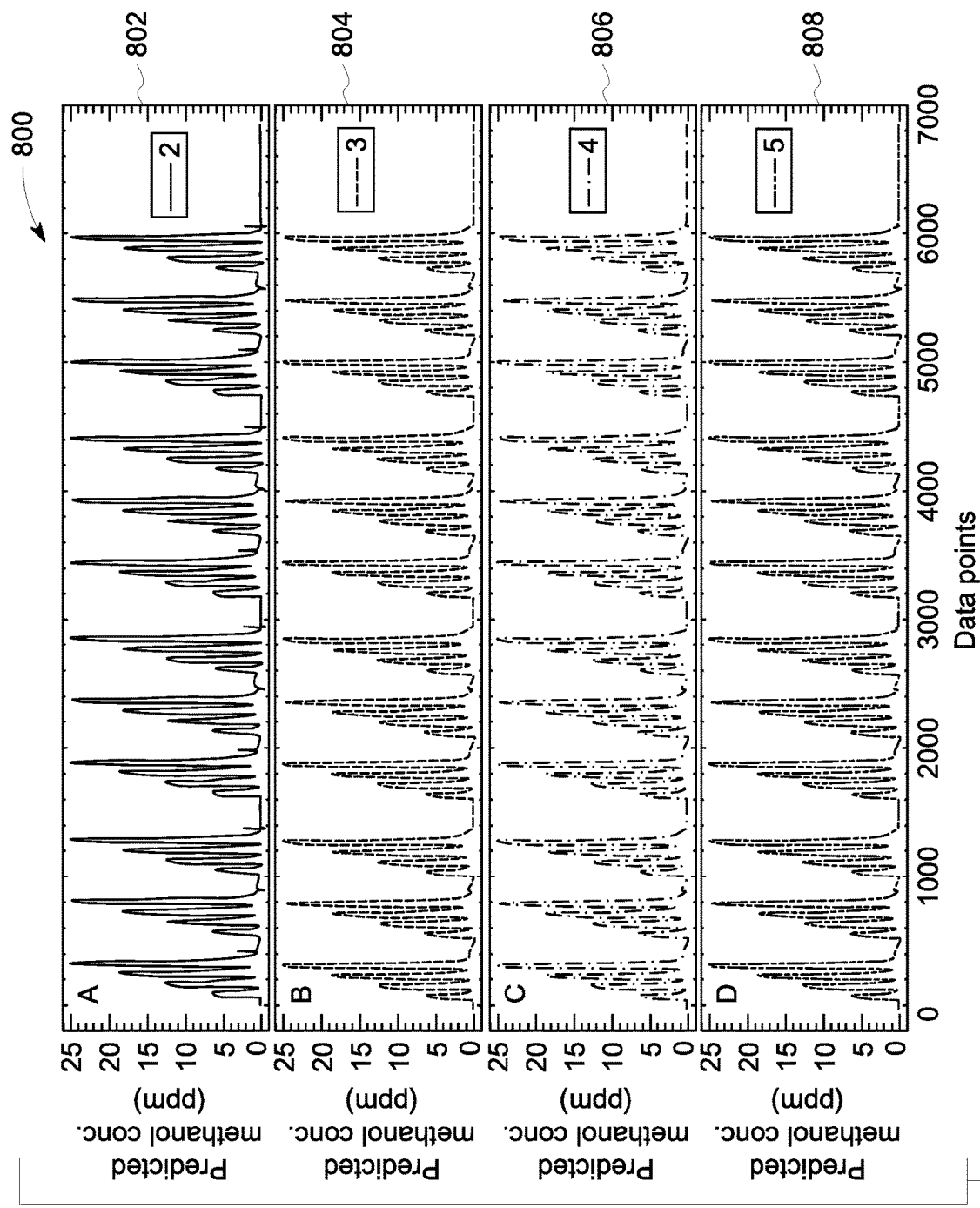
FIG. 10 is a series of plots depicting predictions of generated calibration functions for the different combinations of relative humidity and concentrations of methanol vapor to which the sensor was exposed during the validation phase of FIG. 7.

FIG. 9 is a series of plots 700 of calibration results. To generate the calibration function, three data points were extracted for each experimental condition (each combination of relative humidity and concentration of methanol vapor, shown and described with regard to FIG. 5), resulting in 45 data points. A first plot 702 illustrates the concentration of methanol vapor as the experiment proceeds over time. A second plot 704 illustrates the relative humidity as the experiment proceeds over time. A third plot 706 illustrates residual predicted concentration errors of different calibration functions that take into account increasing numbers of frequencies and Z' or Z" as depicted in FIG. 7. That is, the calibration function labeled "2" takes into account the response at 200 kHz and 7.1 MHz, the calibration function labeled "3" takes into account the response at 200 kHz, 7.1 MHz, and 1.26 MHz, the calibration function labeled "4" takes into account the response at 200 kHz, 7.1 MHz, 1.26 MHz, and 3.99 MHz, and the calibration function labeled "5" takes into account the response at 200 kHz, 7.1 MHz, 1.26 MHz, 3.99 MHz, and 710 kHz. It should be noted that all four calibration functions has prediction errors less than 0.2 ppm of methanol vapor. Predictions for the four calibration functions were then generated for the different combinations of relative humidity and concentrations of methanol vapor to which the sensor was exposed during the validation phase 504 shown in FIG. 7 and then compared to the collected experimental data form the validation phase 504. FIG. 10 is a collection of plots 800 for the predictions of each of the calibration functions for the different combinations of relative humidity and concentrations of methanol vapor to which the sensor was exposed during the validation phase 504 shown in FIG. 7. The first plot 802 is for the calibration function labeled "2" that takes into account the response at 200 kHz and 7.1 MHz, the second plot 804 is for the calibration function labeled "3" that takes into account the response at 200 kHz, 7.1 MHz, and 1.26 MHz, the third plot 806 is for the calibration function labeled "4" that takes into account the response at 200 kHz, 7.1 MHz, 1.26 MHz, and 3.99 MHz, and the fourth plot 808 is for the calibration function labeled "5" that takes into account the response at 200 kHz, 7.1 MHz, 1.26 MHz, 3.99 MHz, and 710 kHz. It should be noted that all four calibration functions provide stable predictions of values of methanol vapor concentration with respect to actual experimental values of 6.25 ppm, 12.50 ppm, 18.75 ppm, and 25.00 ppm over four replicates of the experiment. Further, all calibration functions provide stable prediction of baseline (0 ppm methanol) including at the beginning and the end of the experiment. It should also be noted that the effects of step changes in humidity during the experiment are most pronounced in the predicted values from calibration function "2" that utilizes only two frequencies as small response spikes. However, these spikes were not present in the predicted values from calibration functions "3", "4", and "5" that consider three, four, or five frequencies, respectively. Thus, this data proves that a simple calibration function that utilizes only two response frequencies from the impedance response was adequate to provide a residual error of concentration prediction of less than 0.2 ppm of methanol vapor. As such, a gas sensor having an analog gas sensing element and an analog interferent-compensating sensing element, such as a relative humidity sensing element, disposed in parallel in a single electrical sensing circuit, may be utilized to detect conditions in the monitored environment around the gas sensor, and correct for the detected variations in these conditions to accurately identify identities and/or concentrations of analyte gases in the monitored environment, despite the detected conditions in the monitored environment around the gas sensor.

Technical effects of this disclosure include enabling correction for ambient conditions (e.g., relative humidity, temperature, atmospheric pressure) around gas sensor. Using the disclosed techniques, a MOS-based gas sensor can be designed, manufactured, and used to resolve a plurality of gases in the monitored environment in wider range of atmospheric conditions. Specifically, an analog interferent-compensating sensing element disposed in the same electrical circuit as the gas sensing element may be used to determine one or more atmospheric conditions of the monitored environment around the gas sensor. The response of the sensor to dielectric excitation may then be corrected, based on the determined atmospheric conditions, to determine identities and/or concentrations of gases present in monitored environment. Accordingly, by utilizing the presently disclosed techniques, a sensor may continue to be used and output reliable results in a wider range of monitored environments.

This written description uses examples to disclose the claimed subject matter, including the best mode, and also to enable any person skilled in the art to practice the disclosed subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A sensor for analysis of at least one gas within a monitored environment, comprising:
   a sensing circuit, comprising:
      a gas sensor configured to contact the monitored environment; and
      an interferent-compensating sensor configured to contact the monitored environment, wherein the gas sensor and the interferent-compensating sensor are electrically coupled to one another in parallel, wherein the sensing circuit is configured to provide a single output; and
   an impedance detector configured to:
      provide dielectric excitation of the gas sensor and the interferent-compensating sensor at a set of frequencies;
      measure combined impedance response of the gas sensor and the interferent-compensating sensor to the dielectric excitation at the set of frequencies; and
      determine, based on the combined impedance response of the gas sensor and the interferent-compensating sensor to the dielectric excitation at the set of frequencies, identities, respective concentrations, or a combination thereof, of at least one analyte gas of the monitored environment, corrected for one or more sensed interferent conditions in the monitored environment.

2. The sensor of claim 1, wherein the interferent-compensating sensor comprises a humidity sensor, a pressure sensor, a temperature sensor, or any combination thereof.

3. The sensor of claim 1, wherein the gas sensor comprises a metal oxide semiconductor (MOS) sensing material.

4. The sensor of claim 1, wherein determining the identities, the respective concentrations, or the combination thereof, of the at least one analyte gas of the monitored environment, corrected for the one or more sensed conditions of the monitored environment comprises:
   selecting two or more frequencies from the set of frequencies;
   analyzing the combined impedance response of the gas sensor and the interferent-compensating sensor to the dielectric excitation at the two or more frequencies selected from the set of frequencies to determine the one or more sensed interferent conditions of the monitored environment;
   generating a transfer function to correct the impedance response of the sensor to the at least one analyte gas of the monitored environment for the one or more sensed interferent conditions of the monitored environment; and
   applying the transfer function to correct the impedance response of the sensor to the at least one analyte gas of the monitored environment for the one or more sensed interferent conditions of the monitored environment to the dielectric excitation at the two or more frequencies selected from the set of frequencies to determine the identities, the respective concentrations, or the combination thereof, of the at least one analyte gas of the monitored environment, corrected for the one or more sensed interferent conditions of the monitored environment.

5. The sensor of claim 1, wherein the interferent-compensating sensor is a capacitor, a resistor, or a two-terminal electrical component, or any combination thereof.

6. The sensor of claim 1, wherein the interferent-compensating sensor is an ambient environment sensor.

7. The sensor of claim 1, wherein the at least one analyte gas of the monitored environment comprises gases indicative of indoor air quality, outdoor air quality, urban air pollution, transportation cabin air quality, transportation exhausts, industrial safety, homeland security, medical diagnostics, food freshness, product quality, breath analysis, breath biomarkers, or any combination thereof.

8. The sensor of claim 1, wherein the at least one analyte gas in the monitored environment comprises inorganic gases, organic gases, organic vapors, oxidizing gases, reducing gases, non-condensable gases, vapors, volatile organic compounds, or any combination thereof.

9. The sensor of claim 1, wherein the at least one analyte gas in the monitored environment comprises chemical agents, combustible gases, volatile precursors of fabrication of narcotics and substances, volatile precursors of fabrication of explosives, or any combination thereof.

10. The sensor of claim 1, wherein the sensor is wearable, ingestible, drone-deployable, tattooable, stationary, mobile, wireless, wired, or any combination thereof.

11. The sensor of claim 1, wherein the sensor is integrated into a mobile electronic device, integrated into a medical physiological electronic device, integrated into an audio headset electronic device, integrated into a piece of textile, or any combination thereof.

12. A method of operating a sensor, comprising:
exposing the sensor to a monitored environment;
providing, via an impedance detector, to a sensing circuit comprising a gas sensor and a humidity sensor, a dielectric excitation of the gas sensor and the humidity sensor at a set of frequencies, wherein the gas sensor and the humidity sensor are electrically coupled to one another in parallel, wherein the sensing circuit is configured to provide a single output;
measuring responses of the sensing circuit to the dielectric excitation at the set of frequencies;
determining, based on the responses of the sensing circuit to the dielectric excitation, a relative humidity of the monitored environment; and
determining, based on the responses of the sensing circuit to the dielectric excitation, identities, respective concentrations, or a combination thereof, of at least one analyte gas of the monitored environment, corrected for the determined relative humidity of the monitored environment.

13. The method of claim 12, further comprising:
selecting two or more frequencies from the set of frequencies;
generating a transfer function to correct the responses of the sensing circuit to the dielectric excitation at the two or more frequencies selected from the set of frequencies, based on the determined relative humidity of the monitored environment; and
applying the transfer function to the responses of the sensing circuit to the dielectric excitation at the two or more frequencies selected from the set of frequencies to determine the identities, the respective concentrations, or the combination thereof, of the at least one analyte gas of the monitored environment, corrected for the determined relative humidity of the monitored environment.

14. The method of claim 13, wherein selecting the two or more frequencies from the set of frequencies comprises selecting first and second frequencies at which at least one of the responses of the gas sensor to the concentration of the analyte gas is substantially linear.

15. A sensor for analysis of at least one gas within a monitored environment, comprising:
a sensing circuit, comprising:
a gas sensor configured to contact the monitored environment; and
an interferent-compensating sensor configured to contact the monitored environment, wherein the gas sensor and the interferent-compensating sensor are electrically coupled to one another in parallel, wherein the sensing circuit is configured to provide a single output; and
an impedance detector configured to:
provide dielectric excitation of the sensing circuit at a set of frequencies;
measure impedance response of the sensing circuit to the dielectric excitation at the set of frequencies; and
determine, based on the impedance response of the sensing circuit to the dielectric excitation at the set of frequencies, identities, respective concentrations, or a combination thereof, of at least one analyte gas of the monitored environment, corrected for one or more sensed interferent conditions of the monitored environment.

16. The sensor of claim 15, wherein the interferent-compensating sensor comprises a humidity sensor, a pressure sensor, a temperature sensor, or any combination thereof.

17. The sensor of claim 15, wherein determining the identities, the respective concentrations, or the combination thereof, of the at least one analyte gas of the monitored environment, corrected for the one or more sensed conditions of the monitored environment comprises:
selecting two or more frequencies from the set of frequencies;
analyzing the impedance response of the sensing circuit to the dielectric excitation at the two or more frequencies selected from the set of frequencies to determine the one or more sensed interferent conditions of the monitored environment;
generating a transfer function to correct an impedance response of the gas sensor to the at least one analyte gas of the monitored environment for the one or more sensed interferent conditions of the monitored environment; and
applying the transfer function to correct the impedance response of the sensor to the at least one analyte gas of the monitored environment for the one or more sensed interferent conditions of the monitored environment to the dielectric excitation at the two or more frequencies selected from the set of frequencies to determine the identities, the respective concentrations, or the combination thereof, of the at least one analyte gas of the monitored environment, corrected for the one or more sensed interferent conditions of the monitored environment.

18. The sensor of claim 15, wherein the interferent-compensating sensor is a capacitor, a resistor, or a two-terminal electrical component, or any combination thereof.

* * * * *